(12) United States Patent
Vogel et al.

(10) Patent No.: US 6,564,155 B2
(45) Date of Patent: May 13, 2003

(54) METHOD OF, AND SENSOR FOR, TESTING LIQUIDS

(75) Inventors: Albrecht Vogel, Stutensee (DE); Dieter Binz, Hirschberg (DE); Peter Krippner, Karlsruhe (DE); Sean Keeping, Surrey (DE)

(73) Assignee: ABB Patent GmbH, Ladenburg (DE)

( * ) Notice: Subject to any disclaimer, the term of this patent is extended or adjusted under 35 U.S.C. 154(b) by 0 days.

(21) Appl. No.: 09/910,744

(22) Filed: Jul. 23, 2001

(65) Prior Publication Data

US 2002/0022934 A1 Feb. 21, 2002

(30) Foreign Application Priority Data

Jul. 21, 2000 (DE) .......................... 100 35 911

(51) Int. Cl.$^7$ ............................................ G01N 31/00
(52) U.S. Cl. ..................... 702/25; 702/22; 422/50; 422/56; 422/63; 436/43; 436/127; 436/169
(58) Field of Search ............... 702/25, 19, 22, 702/23; 422/63, 100, 81, 62, 82.01, 82.04, 50, 56, 82.03; 436/127, 138, 163, 169, 181, 43; 700/266

(56) References Cited

U.S. PATENT DOCUMENTS

| 4,318,885 | A | * | 3/1982 | Suzuki et al. ............. 134/22.12 |
| 5,049,358 | A | * | 9/1991 | Lau ............................. 422/56 |
| 5,077,222 | A | * | 12/1991 | Lau ............................. 422/56 |
| 5,428,993 | A | * | 7/1995 | Kobashi ..................... 222/58 |
| 5,993,742 | A | * | 11/1999 | Binz et al. .................... 422/62 |

OTHER PUBLICATIONS

"The pH and conductivity" Omega handbook (1995, vol.29), pp. G–15–G–20.*

* cited by examiner

Primary Examiner—Bryan Bui
Assistant Examiner—Hien Vo
(74) Attorney, Agent, or Firm—Laurence A. Greenberg; Werner H. Stemer; Ralph E. Locher

(57) ABSTRACT

A method and an apparatus tests liquids. When the method is implemented, following a reaction of constituents in the liquid with the maximum quantity at least of one free oxidizing agent and/or reagent contained in the liquid, the quantity of oxidizing agent and/or reagent remaining in the liquid is displayed visually as a measure of the quantity of constituents in the liquid reacting with the oxidizing agent and/or reagent. For implementing the method, use is made of a sensor that is configured as a sheet-like structural element and is provided with at least one inlet opening, a sample-accommodating channel, a mechanical pump, a transporting capillary, a detection zone, an emptying channel, and an outlet opening.

8 Claims, 3 Drawing Sheets

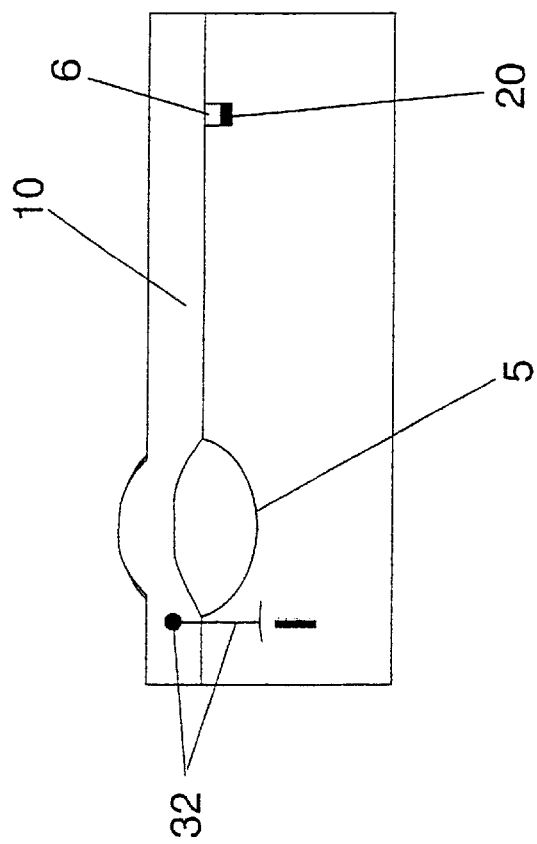
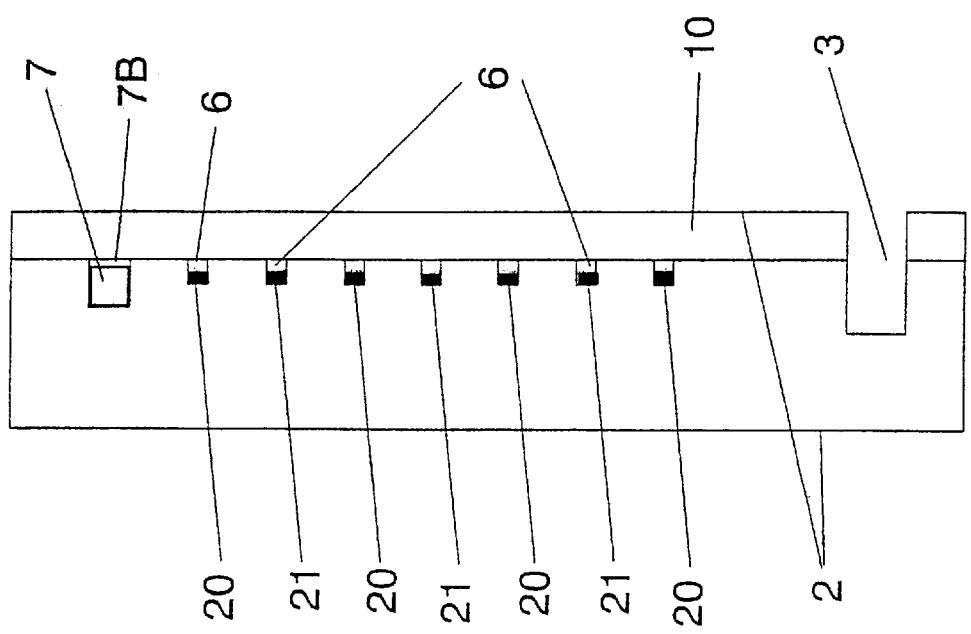

METHOD OF, AND SENSOR FOR, TESTING LIQUIDS

BACKGROUND OF THE INVENTION

Field of the Invention

The invention relates to a method of, and an apparatus for, testing liquids.

Such a method and such an apparatus are used, in particular, for monitoring liquids in clarification plants.

Until now, calorimetric test apparatuses have tested liquids. Calorimetric test apparatuses include a test vessel, a precisely weighed mixture of chemical reagents in solid or liquid form. The composition of the mixture is selected optimally for the measuring task, and an evaluation and display unit. For carrying out the test, a small quantity of the liquid that is to be tested is introduced into the vessel, mixed with the reagents, agitated or, as appropriate, additionally heated. This produces a color reaction. The intensity of the color reaction characterizes the component in the liquid that is to be detected. The color intensity is determined by the evaluation and display unit and converted into a concentration of the sought substance. The disadvantages with this type of liquid testing are the relatively complicated measurement procedure, which requires the user to have laboratory skills, and the high cost of the evaluation and display unit.

Paper-based, or plastic-based test strips are also prior art. In the case of the test strips, certain chemical reagents, specific to the substance that is to be detected, are applied to an end of the paper. The test strips are immersed in the liquid that is to be tested. If a not inconsiderable content of the sought substance is contained in the liquid, it produces, with the reagents on the paper, a color reaction, of which the intensity is a measure of the concentration of the sought substance in the liquid. There is no need to take a sample; the test strip can be immersed directly in the liquid that is to be tested. The pH test sticks constitute a very well known example of this type of liquid testing. The disadvantage with the test sticks is that only straightforward ion-selective reactions can be realized. Biological parameters such as the biological oxygen demand or more complex chemical parameters such as the chemical oxygen demand of a liquid cannot be determined therewith.

Also small compact analysis systems with a volume of approximately 50 $cm^3$ are prior art. The liquid that is to be tested is introduced with a pipette. The analysis system is then disposed in a separate external evaluation and display unit. This unit contains apparatuses in the form of mechanical and/or electroosmotic pumps, with the aid of which the liquid samples can be moved through tunnels in the analysis system. Moreover, the unit provides the auxiliary energy for detecting the sought components. Electrochemical and/or visual detection methods are implemented in the evaluation. A considerable amount of auxiliary energy is required for this purpose. The disadvantage with this type of liquid testing is that an expensive and complicated external evaluation and display unit is required.

SUMMARY OF THE INVENTION

It is accordingly an object of the invention to provide a method of, and sensor for, testing liquids that overcomes the hereinafore-mentioned disadvantages of the heretofore-known methods and devices of this general type and that makes it possible to test liquid more straightforwardly and, in addition, cost-effectively than has been the case hitherto.

With the foregoing and other objects in view, there is provided, in accordance with the invention, a method of monitoring liquids. The method includes sampling a liquid containing constituents. The next step is dissolving a maximum amount of a reagent in the liquid. The next step is reacting the reagent with the constituents to produce a remaining amount of the reagent. The next step is visually detecting the remaining amount of the reagent. The next step is correlating the detected remaining amount of the reagent with a quantity of the constituents.

With the objects of the invention in view, there is also provided a sensor for monitoring liquids. The sensor includes a sheet-like structural element with an inlet opening, a sample-accommodating channel, a mechanical pump, a transporting capillary, a detection zone, an emptying channel, and an outlet opening.

The invention described hereinbelow overcomes the disadvantage of the prior-art configurations. It discloses a liquid sensor that is inexpensive to produce, is easy to use, is intended preferably for a single use, and does not require any external evaluation unit. The sensor makes possible, inter alia, a quick semi-quantitative analysis for determining the biological or the chemical oxygen demand of a liquid. It supplies application-specific information about the state of a liquid. Following the measurement, the sensor is disposed of. Possible fields of use of the invention are, for example, small, decentralized clarification plants without extensive instrumentation for monitoring the water quality. Even unskilled personnel can accomplish this monitoring by using the sensor according to the invention. It is also possible for the sensor to be used, for example, in the process control in drinks manufacturing.

The sensor is of the size of a credit card, it is not more than 5 mm in thickness and has a surface area of 5×8 $cm^2$. A straightforward mechanical pressure pump that is activated by a membrane being subjected to finger pressure transports the liquid sample. The liquid is then transported by capillary action through the interior of the sensor to an outlet opening. Provided within the sensor, at certain locations, are small deposits of reagents that dissolve in the liquid as the latter flows past and trigger the corresponding chemical detection reaction. Also disposed in the sensor are enzymes or catalysts that accelerate a certain chemical detection reaction. The detection reactions are selected such that the result is displayed visually by the change in color on color indicators. The changes in color can easily be seen with the naked eye without any exterior assistance being used. The duration of an analysis is from two to five minutes (2–5 min.).

Other features which are considered as characteristic for the invention are set forth in the appended claims.

Although the invention is illustrated and described herein as embodied in a method of, and sensor for, testing liquids, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 2 is a side view showing the sensor according to FIG. 1 in vertical section along line II—II;

FIG. 3 is a view showing the sensor according to FIG. 1 in vertical section along line III—III.

DESCRIPTION OF THE PREFERRED EMBODIMENTS

Figure 1:
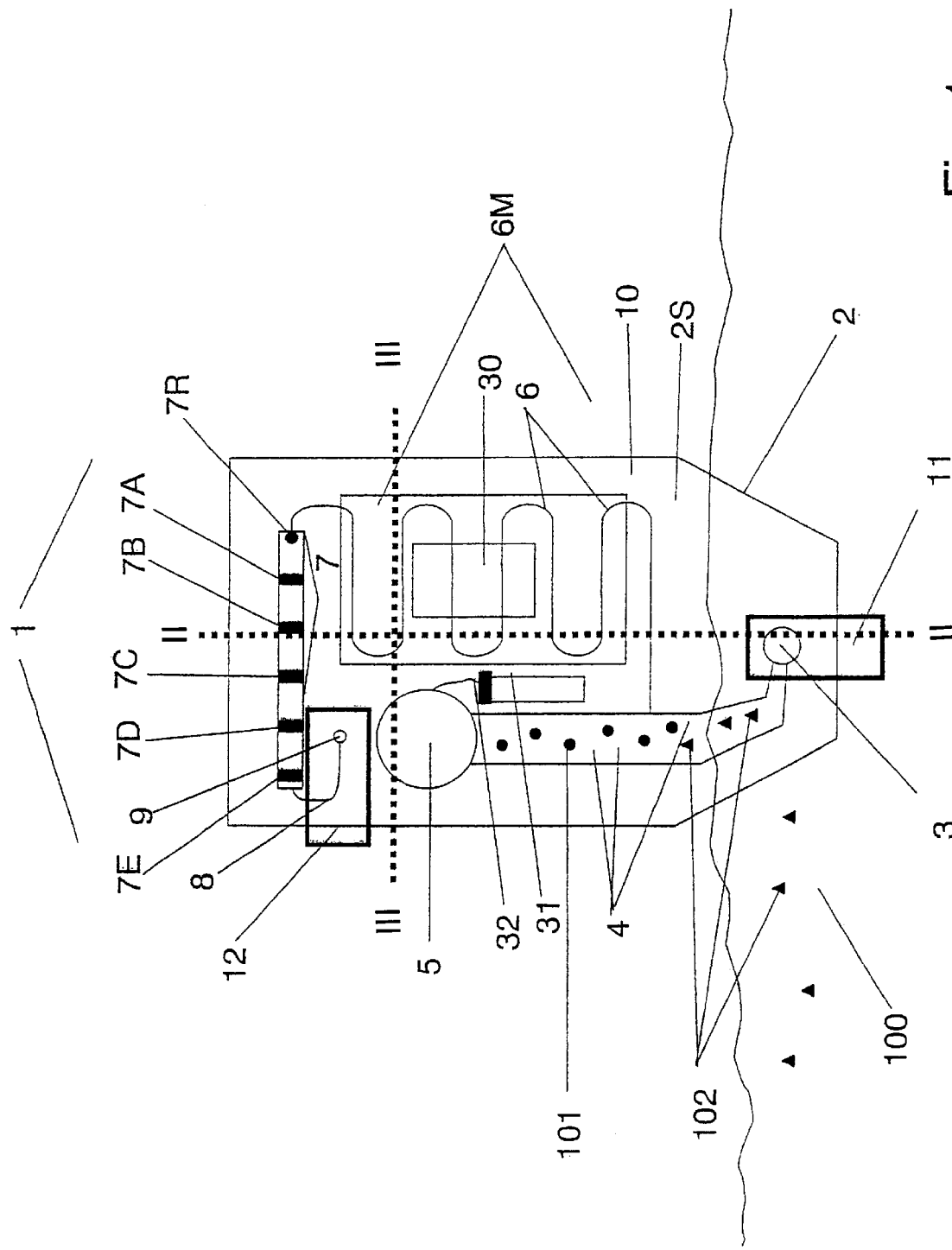
FIG. 1 is a diagrammatic, plan view of a sensor for the analysis of liquids.

In all the figures of the drawing, sub-features and integral parts that correspond to one another bear the same reference symbol in each case.

Referring now to the figures of the drawings in detail and first, particularly to FIG. 1 thereof, there is shown a sensor 1 is formed by a sheet-like structural element 2 made of plastic, ceramic material, or silicon. The thickness of the sheet-like structural element 2 is approximately five millimeters (~5 mm). In the exemplary embodiment illustrated here, the surface 2S of the structural element has an area of 5×8 $cm^2$. If required, the structural element can be of larger or smaller configuration. The sensor 1 is provided with an inlet opening 3. Via this inlet opening 3, a defined quantity of a liquid 100 can be introduced into a sample-accommodating channel 4. The sample-accommodating channel 4 directly adjoins the inlet opening 3. A mechanical pump 5 is integrated in the sample-accommodating channel 4. The pump is formed by a cutout in the surface 2S and a sheet material 10 stretched over the same as is illustrated in FIG. 3. A transporting capillary 6 branches off from the sample-accommodating channel 4. In the exemplary embodiment illustrated here, the transporting capillary 6 meanders. The transporting capillary 6 opens out into a detection zone 7. Since the transporting capillary 6 is very narrow, additional auxiliary transports in the form of a filter paper or fibers (not illustrated here) can be disposed between the transporting capillary 6 and the detection zone 7. These ensure that all the liquid 100 passes out of the transporting capillary 6 into the detection zone 7.

The detection zone 7 is configured as a channel with a length of two centimeters (2 cm) and a width of one-half centimeter (0.5 cm). As FIG. 1 shows, a reagent 7R is disposed downstream of the inlet opening of the detection zone 7. Color indicators 7A, 7B, 7C, 7D, 7E are disposed at a defined distance apart within the detection zone 7. From the detection zone 7, the liquid 100 is fed to an outlet opening 9 via an emptying channel 8. As can be gathered from FIGS. 2 and 3, the inlet opening 3, the sample-accommodating channel 4, the pump 5, the transporting capillary 6, the detection zone 7, the emptying channel 8, and the outlet opening 9 are all formed by cutouts which are produced with defined dimensions in the structural element 2 by etching or grooving. In the exemplary embodiment illustrated here, the diameter of the inlet opening 3 is three millimeters (3 mm).

The sample-accommodating channel 4 has a diameter of six-tenths of a millimeter (0.6 cm). The pump 5 has a diameter of one centimeter (1 cm). The transporting capillary 6 has a diameter of fifty microns (50 µm), while it has a length of four centimeters (4 cm). The diameter of the outlet opening is one millimeter (1 mm).

In order that the liquid 100 can only pass into the structural element 2 via the inlet opening 3, and can also only leave the structural element via the outlet opening 9, the surface of the structural element 2 is covered permanently by sheet material 10, at least in the regions in which the sample-accommodating channel 4, the pump 5, the transporting capillary 6, the detection zone 7, and the outlet channel 8 are located, such that the liquid 100 also cannot be distributed over the structural element 2 beneath the sheet material 10. Over the sample accommodating channel 4, the sheet material 10 is formed such that it is permeable to oxygen. A separate sheet material 11 respectively closes off the inlet opening 3 and the outlet opening 9, 12, these being removed when operation of the sensor 1 commences. As FIG. 2 shows, the base of the transporting capillary 6 is coated in the central region 6M of the transporting capillary, with enzymes 20 and/or catalysts 21.

A small heating element 30 is additionally integrated in the central region 6M of the transporting capillary 6. This allows this part of the transporting capillary 6 to be heated locally to temperatures of up to a maximum of one hundred degrees Celsius (100 C.). For the power supply, a small flat battery cell 31 with a straightforward small circuit (not illustrated here) for temperature regulation and with a miniaturized temperature sensor is likewise accommodated in the structural element 2. A pressure sensor 32 is led from the battery 31 to the pump 5, as is illustrated in FIGS. 1 and 3. Upon actuation of the pump 5, heating of the region 6M is thus also started. This accelerates the chemical detection reactions in the transporting capillary 6.

Instead of heating element 30, it is also possible to provide an additional chamber (not illustrated here) on or within the structural element 2. Disposed in the chamber are two chemical elements or compounds which, when mixed, react exothermically with one another. First of all, however, a membrane separates them from one another. The membrane is severed by one pressing on the chamber. During the chemical reaction that then takes place, heat is released. This heat heats the central region 6M of the transporting capillary 6 to such an extent that the chemical reactions in the transporting capillary 6 are accelerated as a result.

In order to determine the biological oxygen demand of the liquid 100 using the sensor 1, first of all the sheet material 11 over the inlet opening 3 is removed. The structural element 2 is then immersed to such an extent in the liquid 100 that is to be tested that the inlet opening 3 is completely covered by liquid 100, although the outlet opening 9 and the pump 5 are not. Pressing on the pump 5 removes the air that may possibly be contained in the sample-accommodating channel 4. The sheet material 10 over the sample-accommodating channel 4 is formed to be elastic and gas-permeable, with the result that the liquid 100 can become saturated with oxygen 101. For this purpose, use may be made, for example, of a sheet material 10 made of silicone or polytetrafluoroethylene. When the pump 5 is released, the sheet material 10 moves back into its starting position again. By virtue of the vacuum that has formed in the sample-accommodating channel 4, liquid 100 is sucked into the sample-accommodating channel 4. If required, the inlet opening 3 may be provided with a filter (not illustrated here), which preferably has a pore size of two-tents of a micron (0.2 µm) and thus protects the inlet opening 3 and the sample-accommodating channel 4 against blockage. The sheet material 12 over the opening outlet 9 is then removed. During the time over which the liquid 100 is located in the sample-accommodating channel 4, it takes up a maximum possible quantity of four milligrams per liter (4 mg/l) of oxygen 101. From the sample-accommodating channel 4, the liquid 100 is sucked by capillary action into the transporting capillary 6. From there, it moves into the detection zone 7 and the emptying channel 8 until it reaches the outlet opening 9. As has already been mentioned, the transporting capillary 6 is coated in the central region 6M, with enzymes 20 and/or catalysts 21. The enzymes 20 and/or the catalysts 21 cause the organic molecules 102 in the form of glucose, fructose, and/or lactose which are contained in the liquid 100 to react with the free oxygen 101 which is contained in the liquid 100. During this reaction, oxygen 101 is used up, heat is released, and biomass (not illustrated here) is formed. A certain enzyme 20 or a certain catalyst 21 in each case is suitable for reacting with a certain molecule, for example glucose, fructose, or lactose. Since the fullest possible range of molecules is to be covered, a mixture of from six to ten (6–10) different enzymes 20 or catalysts 21 are provided. From the transporting capillary 6, the liquid 100 passes automatically into the detection zone 7. There, the free oxygen that is still contained in the liquid 100 is determined.

One or more reagents 7R in the form of salts are disposed in the detection zone 7, directly downstream of the inlet opening of the latter. For this purpose, use is made of, for example, manganese dichloride and/or potassium iodide. These reagents 7R dissolve when the liquid 100 flows past them. Downstream of the reagents 7R, as seen in the flow direction, color indicators 7A, 7B, 7C, 7D, and 7E are disposed at a defined distance apart from one another. A change in color of the color indicators 7A, 7B, 7C, 7D, 7E is triggered by the reagent 7R and free oxygen in the liquid 100. The color indicators 7A, 7B, 7C, 7D, 7E display a green color, for example, before operation of the sensor 1 commences. By the action of the reagent 7R and of the free oxygen, the color of the color indicators 7A, 7B, 7C, 7D, 7E changes to red. The color indicators 7A, 7B, 7C, 7D, 7E are configured as threshold indicators. The change in color only takes place if the content of free oxygen in the liquid 100, in conjunction with the dissolved reagent 7R exceeds a certain value. If the content of oxygen remains below this value, then the color indicators 7A, 7B, 7C, 7D, 7E do not change color. This means that, during the reaction in the transporting capillary 6, all, or virtually all of the free oxygen in the liquid has been used up in order to convert the organic molecules contained in the liquid 100 into heat and biomass. The color indicators 7A, 7B, 7C, 7D, 7E are configured and disposed such that an increasing detection threshold can be observed from right to left. This means that the color indicator 7A reacts in the case of a content of one-tenth of milligram per liter (0.1 mg/l) of free oxygen, the color indicator 7B reacts in the case of a content of five-tenths of a milligram per liter (0.5 mg/l), the color indicator 7C reacts in the case of a content of one milligram per liter (1 mg/l), the color indicator 7D reacts in the case of a content of two milligrams per liter (2 mg/l) and the color indicator 7E reacts in the case of a content of four milligrams per liter (4 mg/l). If, then, for example the color indicators 7A, 7B, and 7C respond, this means that the content of free oxygen in the liquid 100 is greater than one milligram per liter (>1 mg/l) but smaller than two milligrams per liters (<2 mg/l). Because the oxygen content in the sample-accommodating channel 4 has a saturation value of four milligrams per liter (4 mg/l), the change in color of one or more color indicators in the detection zone 7 can be evaluated as a measure of the biological oxygen demand of the liquid 100.

Figure 4:
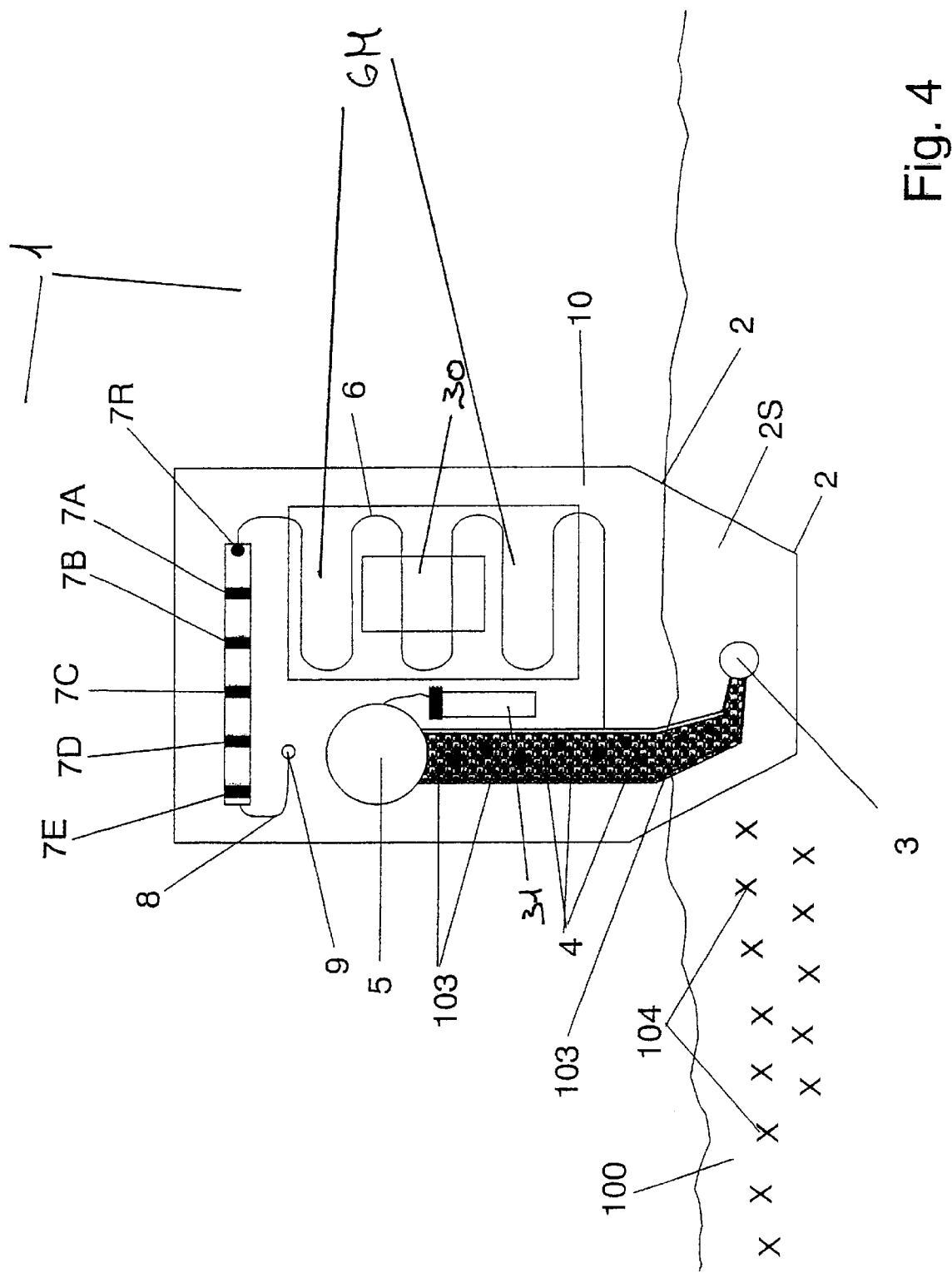
FIG. 4 is a plan view of an alternate embodiment of the sensor illustrated in FIG. 1.

FIG. 4 shows a variant of the sensor 1 illustrated in FIG. 1, which can be utilized for measuring the chemical oxygen demand in the liquid 100. The two sensors 1 are of essentially identical construction. Identical components are thus designated identically. The sensor 1 is formed in this case, too, by a sheet-like structural element 2. In the exemplary embodiment illustrated here, a reagent substance in the form of a salt 103 is disposed between the sheet material 10 and the sample-accommodating channel 4, which is covered over by the sheet material. The reagent substance 103 acts as a strong oxidizing agent. If the liquid 100 flows into the sample-accommodating channel 4 following the removal of the sheet materials 11 and 12 from the inlet opening 3 and the outlet opening 9 and the release of pressure on the pump 5, then the salt 103 dissolves in the liquid 100. As the liquid 100 continues on its way, mixed with the dissolved salt 103, a chemical oxidation of the oxidizable constituents 104 of the liquid 100 takes place in the central region 6M of the transporting capillary 6. The activation energy for this chemical oxidation is reduced by the catalysts 21 applied to the base of the transporting capillary 6, in the central region 6M thereof, according to FIG. 2, with the result that the oxidation can also take place at ambient temperature. The oxidizing agent remaining in the liquid is then detected in the detection zone 7. This takes place as has been explained in the description relating to FIG. 1. Also disposed here, downstream of the inlet of the detection zone 7, is a reagent 7R, which is dissolved in the liquid 100. Together with the oxidizing agent, the reagent causes a change in color in one or more color indicators 7A, 7B, 7C, 7D, 7E in dependence on the quantity of oxidizing agent in the liquid 100. This means that the remaining quantity of oxidizing agent can be determined easily since the quantity of oxidizing agent that was added originally is known. That is the quantity of salts 103 that has dissolved in the liquid 100. The sensor 1 may also be used for detecting the pH or the ion content in water. All that takes place in this case is mixing of the water with a reagent 7R in the detection zone 7 and the detection by changes in color of the color indicators 7A, 7B, 7C, 7D, 7E. Oxidizing agents, enzymes and catalysts may be dispensed with. In this case, the transporting capillary 6 only serves for transporting the liquid.

The use of the sensor 1 according to the invention is not just Unrestricted to the exemplary embodiment described above; rather, all the possible applications for which the sensor 1 is suitable are included.

We claim:

1. A method of monitoring liquids, which comprises:
    sampling a liquid containing constituents;
    dissolving a maximum amount of oxygen in the liquid;
    reacting the oxygen with the constituents to produce a remaining amount of free oxygen in the liquid;
    quantitatively coloring the remaining amount of the free oxygen in the liquid; and
    correlating the detected remaining amount of the free oxygen in the liquid with a quantity of the constituents.

2. The method according to claim 1, which comprises, after reacting the oxygen with the constituents, reacting the free oxygen with a color indicator.

3. The method according to claim 1, wherein the color indicator has a threshold concentration and the amount of said free oxygen must exceed the threshold concentration to react.

4. A sensor for monitoring liquids, comprising:
    a sheet-like structural element with an inlet opening and having a surface;
    a sample-accommodating channel connected to said inlet opening;
    a mechanical pump integrated in said sample-accommodating channel;
    a transporting capillary having two opposing ends and a central region therebetween, a first of said ends being connected to said sample-accommodating channel, said transporting capillary being configured in a meandering fashion, said central region having a catalyst applied thereto;

a detection zone being formed as a channel and having an inlet connected to a second of said ends of said transporting capillary, an outlet, a reagent downstream of said inlet, and at least two color indicators downstream of said reagent and spaced from each other at a defined distance;

an emptying channel connected to said outlet of said detection zone; and an outlet opening connected to said emptying channel;

said inlet opening, said sample-accommodating channel, said mechanical pump, said transporting capillary, said detection zone, said emptying channel, and said outlet opening being formed by cutouts formed in said surface of said structural element;

an elastic, gas-permeable membrane sheet material firmly connected to said surface of said structural element and closing off said cutouts from the outside.

5. The sensor according to claim 4, for monitoring liquids by sampling a liquid containing constituents, dissolving a maximum amount of a reagent in the liquid, reacting said reagent with the constituents to produce a remaining amount of said reagent, visually detecting the remaining amount of said reagent, and correlating the detected remaining amount of said reagent with a quantity of the constituents.

6. The sensor according to claim 4, wherein said catalyst is an enzyme.

7. The sensor according to claim 4, wherein said structural element has a thickness between two and five millimeters, and a surface area between five and eight square centimeters.

8. A method of monitoring liquids, which comprises:

sampling a liquid containing oxidizable constituents;

dissolving a maximum amount of oxygen in the liquid;

fully reacting the oxygen with the oxidizable constituents to yield a remaining amount of free oxygen in the liquid;

quantitatively coloring the remaining amount of free oxygen in the liquid to produce a color; and correlating the color to an oxygen demand of the liquid.

* * * * *